United States Patent [19]

Davies et al.

[11] Patent Number: 5,427,951
[45] Date of Patent: Jun. 27, 1995

[54] DIAGNOSTIC TEST FOR DETERMINING THE ANTIOXIDANT STATUS OF A SAMPLE

[75] Inventors: Michael J. Davies, Burnholme; Catherine A. Rice-Evans, London, both of England

[73] Assignee: British Technology Group Limited, London, England

[21] Appl. No.: 75,532
[22] PCT Filed: Dec. 13, 1991
[86] PCT No.: PCT/GB91/02228
§ 371 Date: Aug. 30, 1993
§ 102(e) Date: Aug. 30, 1993
[87] PCT Pub. No.: WO92/10759
PCT Pub. Date: Jun. 25, 1992

[30] Foreign Application Priority Data
Dec. 14, 1990 [GB] United Kingdom ............... 9027131

[51] Int. Cl.⁶ ............................................. G01N 33/72
[52] U.S. Cl. ................................. 436/66; 436/164; 436/171
[58] Field of Search ................ 436/63, 66, 164, 166, 436/171, 174, 808; 422/61

[56] References Cited

U.S. PATENT DOCUMENTS

| | | | |
|---|---|---|---|
| 3,627,698 | 12/1971 | Rey et al. | 436/66 X |
| 4,071,321 | 1/1978 | Lan | 436/66 |
| 4,189,304 | 2/1980 | Adams, Jr. et al. | 422/56 |
| 4,251,223 | 2/1981 | White | 436/66 |
| 4,556,640 | 12/1985 | Gantzer | 436/66 |
| 4,886,760 | 12/1989 | Ben-Michael | 436/66 |
| 4,891,314 | 1/1990 | Pauly et al. | 436/66 X |
| 4,900,662 | 2/1990 | Shah et al. | 436/811 X |
| 4,954,435 | 9/1990 | Krauth | 435/28 X |
| 4,988,616 | 1/1991 | Heidenreich et al. | 436/66 X |
| 5,081,040 | 1/1992 | Patel et al. | 436/66 |
| 5,089,420 | 2/1992 | Albarella et al. | 436/66 |

FOREIGN PATENT DOCUMENTS 59-222766 12/1984 Japan.
1508165 9/1989 U.S.S.R..

OTHER PUBLICATIONS

American Heart Journal, vol. 105, No. 4, 4/83 pp. 642-651 Drexel et al "Myoglobinemia in the early..-myocardial infarction".
Hochstein, P. "Antioxidant Mechanisms in the Heart. The potential involvement of Myoglobin", pp. 245-252, contained in book by Labbate et al., *Role of oxygen radicals in Cardiovascular Disease*, 1988.

Primary Examiner—James C. Housel
Assistant Examiner—Maureen M. Wallenhorst
Attorney, Agent, or Firm—Nixon & Vanderhye

[57] ABSTRACT

A diagnostic test can determine the occurrence of myocardial infarction or the total plasma antioxidant status as a marker of predisposition to such an event, or the antioxidant status of other clinical and non-clinical samples. The test involves contacting a clinical sample in the presence of myoglobin and an oxidant therefor with a compound which reacts in that environment to form a chromogenic species with a characteristic absorption band in the visible spectrum spaced from potentially interfering bands attributable to haem proteins and other blood components.

7 Claims, 8 Drawing Sheets

DIAGNOSTIC TEST FOR DETERMINING THE ANTIOXIDANT STATUS OF A SAMPLE

This invention relates to a diagnostic test suitable for monitoring the occurrence of a heart attack, or the total plasma antioxidant status as a marker of predisposition to such an event.

The invention therefore arises out of the need to clarify firstly the diagnosis of chest pain in patients as a myocardial infarction and, secondly, the potential for early monitoring of predisposition to heart disease through assessment of total plasma antioxidant capacity.

BACKGROUND OF THE INVENTION

There is a need for means for monitoring plasma antioxidant status, particularly that of a patient believed to be at risk of a heart attack. Further, there is a corresponding need to monitor whether myocardial infarction has actually occurred in a suspect heart attack patient, as it is not always possible for the clinician to distinguish between the experience of chest pains due to less serious disorders and those associated with a heart attack. In both instances, i.e. before or after such an event, knowledge is needed in order to determine the appropriate therapy.

Tests are already known to determine whether myocardial infarction has occurred. Thus it is recognised that such an event causes the early release of the haem protein myoglobin into the plasma (see Drexel et al., American Heart Journal, 105, No. 4, 642-650). The appearance of myoglobin as an indicator of myocardial infarction has been previously determined by radioimmunoassay (Rosano & Kenny, Clin. Chem. 23, 69-75, 1977) and by an agglutination test using a commercially available polystyrene latex sensitised with myoglobin antibodies. The disadvantages of such tests are that radioimmunoassays are time-consuming and thus not suitable for emergency testing, while latex agglutination tests give only semi-quantitative results and can occasionally give false negatives in the presence of antigen excess. It is also possible to detect the leakage of other enzymes such as creatine kinase but these enzymes are released more slowly than myoglobin. The presently available detection kits are costly, lacking in precision or involve time delays so that the diagnosis of a heart attack cannot be confirmed until many hours after the event.

The present invention seeks to provide a test which can be readily performed in a relatively short time period after a suspected heart attack.

In addition it is now known that although free radicals are essential for many normal physiological processes, they can, however, become highly destructive If not tightly controlled. In the normal course of events cells and tissues have adequate antioxidant defences both intracellularly and extracellularly to deal with excess radical generation. However, any pathological situation which increases the turnover of the antioxidant cycle, whether increased oxidative stress or defective anti-radical defences, can lead to progressive membrane, cellular and tissue damage. Free radicals have been implicated in the pathophysiology of many disease states including rheumatoid arthritis, adult respiratory distress syndrome, thalassaemia, reperfusion injury, atherosclerosis and ischaemic heart disease. The formation of oxygen-derived free radicals occurs as an accompaniment to or a consequence of the initial pathology thus exacerabating the primary lesion.

There is also the possibility of further damage occurring at the time of reperfusion. There is now a wide range of evidence linking oxygen-derived free radicals to cardiovascular disease and myocardial post-ischaemic reperfusion injury. Normally, the tissue concentration of active oxygen species is limited and the aerobic myocardium survives because of the existence of a delicate balance between the cellular systems that generate the various oxidants in the normal course of events and those that maintain the antioxidant defence mechanisms.

It will be seen therefore that there is a need to monitor the antioxidant defenses, which may be limited, in disease states or in states which would lead to problems, e.g. pre-term babies. Furthermore, there is a need for ready assessment of the antioxidant status of materials likely to come into contact with human metabolism, such as drugs or foodstuffs.

The invention therefore also seeks to provide a diagnostic test which can be used to monitor the antioxidant status.

DESCRIPTION OF THE INVENTION

Accordingly, the present invention provides a diagnostic test for determining the occurrence of myocardial infarction by means of a clinical sample or the total antioxidant status of a clinical or non-clinical sample comprising contacting the sample in the presence of myoglobin and an oxidant therefor with a compound which reacts in the presence of myoglobin and its oxidant to form a chromogenic species which demonstrates a characteristic absorption band in a region of the visible spectrum spaced from the absorption bands of haem proteins and other constituents of blood and monitoring said absorption band. The monitoring may involve determining the appearance or disappearance of the absorption band and the rate thereof, its intensity, and its duration.

Compounds which react in the presence of myoglobin and hydrogen peroxide to form chromogenic species are preferably 2,2'-azinobis-(3-ethylbenzthiazoline-6-sulphonic acid) (hereinafter referred to as ABTS) or a salt thereof such as the diammonium salt, or 3,5,3'5'-tetramethyl benzidine (hereinafter referred to as TMB). These compounds have been shown to participate in the production of radical cations in the kinetic study of one-electron transfer reactions (see Wolfenden & Willson, Chem. Soc. Perkin Trans. II, 1982, 805-812 and Josephy et al., J. Biol. Chem. 257, 3669-3675, 1982). Other possible compounds based on a fluorimetric assay include luminol (Candy et al., J. Chem. Soc. Perkins Trans. 2, 1385-1388, 1990).

ABTS has been shown to react with hydroxyl radicals to form a radical cation with an absorption maximum in the region of 415 nm, a region which would be interfered with by the presence of a natural chromogen such as a haem protein. However, we have surprisingly found that this compound gives, in the presence of myoglobin and an oxidant therefor, absorption bands centred at 734 nm which are readily distinguishable from the absorption bands attributable to the individual components of the reaction mixture, the presence of blood constituents and the haem protein myoglobin itself. Although not wishing to be bound by any particular theory, it Is believed that the myoglobin molecules present in the system can be activated by an oxidising agent such as hydrogen peroxide to ferryl myoglobin species which themselves can react with ABTS to form a chromogenic ABTS radical cation of sufficient stability for detection of the characteristic absorption band, the intensity of absorption being a function of the amount of available activated myoglobin which is dependent on the amount of myoglobin present in the system and the antioxidant status of the plasma. A similar modus operandi applies to TMB.

When the method of the invention is used to determine the occurrence of myocardial infarction, the clinical sample as obtained from the patient will be derived from blood plasma and, if such an event has occurred, contain myoglobin from disrupted myocytes. At such a site of damage, local generation of superoxide radicals from activated inflammatory cells at the site of injury and their continued presence as a result of the release of chemoattractants from the invading inflammatory cells, can be converted to hydrogen peroxide and a localised interaction between this and myoglobin may occur. Local generation of such ferryl species at specific sites exacerbates the tissue injury. It is this interaction which the test proposed here exploits. The appearance of the ABTS or TMB characteristic bands are therefore indicative of the presence of myoglobin and thus that a heart attack has occurred.

The invention therefore also includes a kit suitable for carrying out a diagnostic test on a clinical sample derived from blood plasma for the determination of the occurrence of myocardial infarction comprising a compound which reacts in the presence of myoglobin and an oxidant therefor to form a chromogenic species having a characteristic absorption band in a region of the visible spectrum distinguishable from the absorption bands of haem proteins and other blood constituents. The compound is preferably ABTS or a salt thereof, although it will be appreciated that alternative compounds may be employed such as tetramethyl benzidine (TMB), or luminol linked to a spectrofluorimetric assay.

When the method of the invention is used to determine the total antioxidant status, for example as a marker of predisposition to an event such as myocardial infarction, the sample may not contain myoglobin. However If it is a clinical sample it will contain some naturally-occurring antioxidants, the depletion of which will depend on the previous history of the patient from whom the sample Is obtained. If it is a non-clinical sample the antioxidant status will depend on the chemical composition of the sample. Therefore a known quantity of myoglobin and oxidant therefor, suitably hydrogen peroxide, are added to the sample before, during or after contact with the ABTS, TMB etc. The magnitude of the subsequent absorption band detected and/or the time lag before such a band appears or the diminution in said band are indicative of the level of antioxidant(s) present in the sample and capable of inhibiting the ABTS or TMB-activated myoglobin interaction.

The invention therefore also includes a kit suitable for carrying out, on a clinical or non-clinical sample, the determination of total antioxidant status, comprising myoglobin, an oxidant therefor (preferably hydrogen peroxide) and a compound which reacts in the presence of myoglobin and the oxidant to form a chromogenic species having a characteristic absorption band in a region of the visible spectrum distinguishable from the absorption bands of haem proteins and other blood components.

The clinical sample may be blood plasma itself or the plasma may have been subjected to pretreatment such as centrifugation for clarification purposes. Alternatively the sample may be of other body acids such as amniotic fluid, synovial fluid, vitreous humour, or urine.

The antioxidant assay may be used clinically as a marker of limited antioxidant defenses in disease states such as heart disease, diabetes, alcoholism, malignant hypertension, respiratory distress and atherosclerosis, or to monitor potential problems, for example in preterm babies, by assay of plasma or other biological fluids. The assay may also be used non-clinically, for example to determine the antioxidant status of drugs or foodstuffs.

The amount of chromogen-producing compound is preferably from 50 $\mu$M to 50 mM for ABTS and from 1 $\mu$M to 1 mM for TMB.

It will be appreciated that tests can be carried out simply and speedily, with a simple spectroscopic measurement being sufficient to provide the required information. Effective therapy can thus be put into effect quickly, whether this be treatment following a diagnosed heart attack or intervention therapy to prevent a heart attack.

It will be appreciated that the order of addition of reactants to the system is not critical. Thus, myoglobin, the detecting compound and the oxidant can be added to blood plasma and the appearance of the characteristic absorption band monitored. Alternatively a system containing myoglobin, its oxidant and the detecting compound can be established exhibiting the characteristic absorption and the blood plasma subsequently added to observe the effect on the absorption of antioxidant present In the plasma.

Several different possible strategies are apparent in the measurement of the antioxidant status of plasma: for example,     a. decolourisation assay     b. inhibition assay (fixed time point)

c. inhibition assay (reaction rate)

d. lag phase measurement

The different options for assay strategy therefore need careful evaluation.

a. the reaction of ABTS with hydrogen peroxide and myoglobin may be allowed to proceed until the colour of the incubation mixture is stable. It is postulated that this reaction occurs in the presence of myoglobin, which acts as a peroxidase, via the formation of a ferryl-myoglobin radical which extracts an electron from the ABTS molecule to give the ABTS radical cation and metmyoglobin. When an aliquot of a plasma sample is added to the reaction mixture, the plasma antioxidants reverse the formation of the ABTS radical cation. The percentage loss of colour (blank - test, measured at 734 nm) or the percentage colour remaining at a given point in time can then be used as an index of plasma antioxidant activity.

b. ABTS, metmyoglobin and the plasma sample may be mixed, and the reaction initiated by the addition of hydrogen peroxide. At a fixed time point the absorbance of the solution is read, along with a buffer blank (with no plasma added and which will therefore have a higher absorbance value than a test solution containing plasma). The development of the ABTS radical will be inhibited to an extent dependent on the plasma antioxidant capacity. The blank absorbance value minus the test absorbance, divided by the blank absorbance (expressed as a percentage) is the percentage inhibition of the reaction. The percentage inhibition is proportional to the antioxidant capacity of the plasma sample. Alternatively, the reaction may be initiated by addition of metmyoglobin, with hydrogen peroxide added at an earlier time point.

c. The procedure outlined in b. is followed, with all the reagents added together and the reaction started with hydrogen peroxide, but the reaction rates of the test and buffer blank are monitored, and a result is derived by comparison of reaction rates rather than absorbance at a fixed time point. It might thus be possible to derive the result at an earlier point in the reaction than by using a fixed time method, and the linearity range of the assay might simultaneously be extended.

d. Sample, metmyoglobin, ABTS and hydrogen peroxide are mixed at time zero, and the time is noted for the development of colour in the cuvette to be initiated. The length of time of the lag phase before the reaction starts Is then proportional to the concentration of antioxidants in the sample.

It has been found particularly suitable to employ method b). Suitable concentrations of myoglobin (as metmyoglobin) range from 0.5 to 5 $\mu$M, preferably about 2.5 $\mu$M, of ABTS of from 25 to 2500 $\mu$M, preferably about 150 $\mu$M and of peroxide of from 12.5 to 1000 $\mu$M, preferably about 75 $\mu$M. The molar ratio of ABTS to oxidant is suitably about 2:1. The assay has been found applicable to samples of down to 50 or even 3 $\mu$l, especially when employing a centrifugal analyser of the Cobas Bio type.

BRIEF DESCRIPTION OF THE DRAWINGS

The invention will now be further illustrated with reference to the following drawings, in which.

EXAMPLES

Example 1

Detection of myoglobin in buffer solution using ABTS

Figure 1:
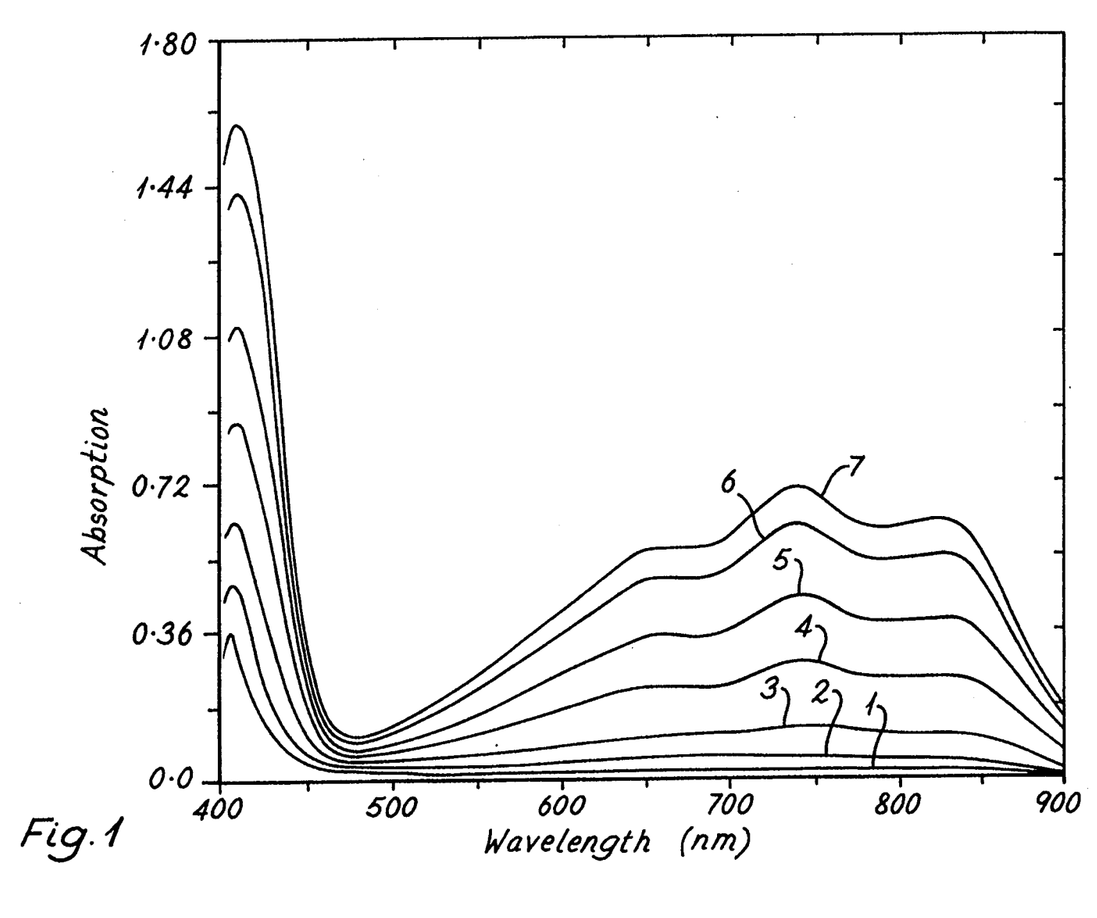
FIG. 1 shows the visible spectra of a solution prepared in accordance with Example 1.

Using phosphate buffer, pH 7.4, two solutions were prepared, a) a control solution containing 2 $\mu$M myoglobin (obtained from Sigma and purified before use) and 2 mM ABTS diammonium salt (obtained from Aldrich) and b) a solution containing 2 $\mu$M myoglobin and 2 mM ABTS to which a 12.5 fold molar excess of $H_2O_2$ was added at zero time to give an $H_2O_2$ concentration of 25 $\mu$M. The visible spectra of a) and b) were determined using a Beckman DU65 or DU70 spectrophotometer at two minute time intervals ranging from 0 to 23 minutes. The results are shown in FIG. 1 for control a) (trace 1) and for b) after 15 sec. (trace 2), 2 min. 15 sec. (trace 3), 6 min. 15 sec. (trace 4), 10 min. 15 sec. (trace 5), 16 min. 15 sec. (trace 6) and 22 min. 15 sec. (trace 7).

The development of a peak at 734 nm stabilizing towards a maximum absorbance greater than 0.72 is clearly demonstrated in FIG. 1.

Example 2

Detection of myoglobin in stored plasma using ABTS

Figure 2A:
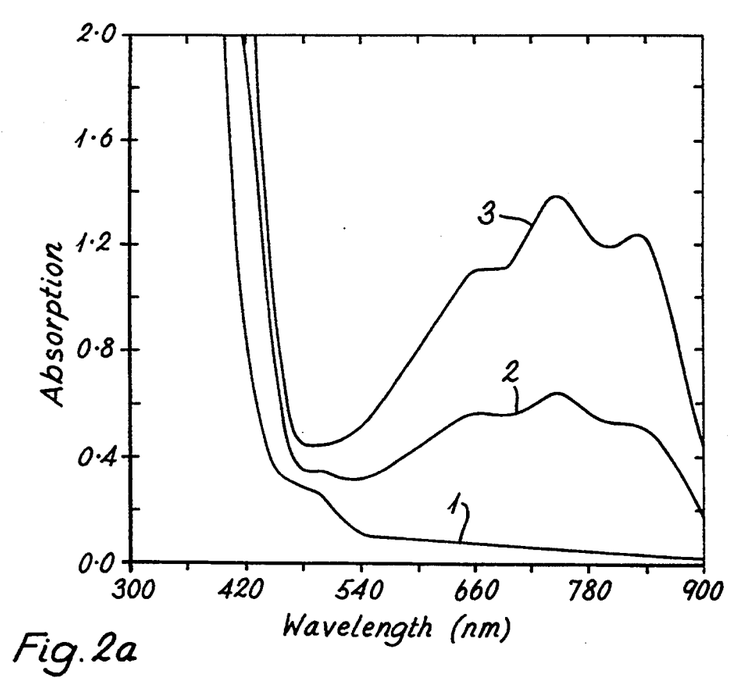
FIGS. 2a and 2b show the visible spectra of a solution prepared in accordance with Example 2.
Figure 2B:
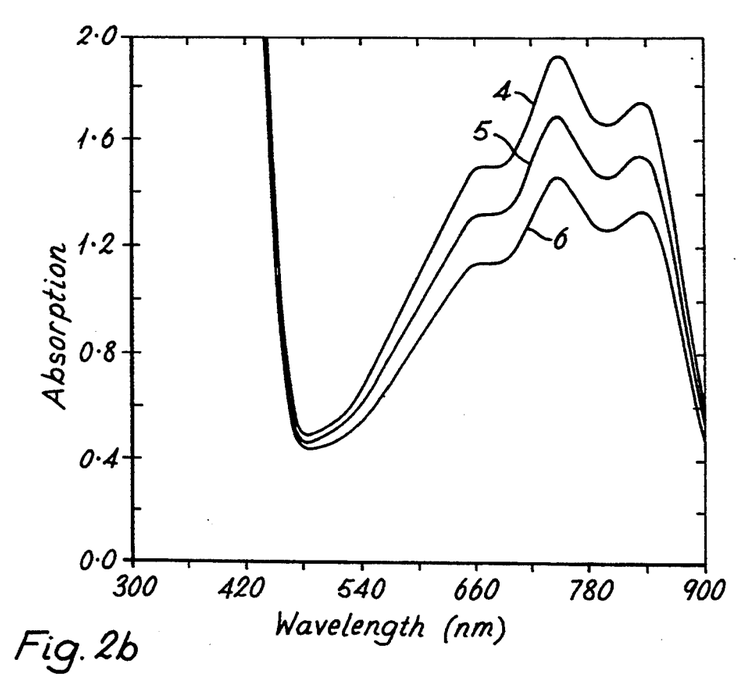

Using blood plasma from a "normal" person, which had first been centrifuged to clarify and stored for 48 hours, a solution was prepared containing 50% by volume plasma in phosphate buffer, 4 $\mu$M myoglobin, 0.5 mM $H_2O_2$ and 16.7 mM ABTS. The spectral characteristics were determined as a function of time and are shown in FIG. 2 a) and b) after 15 sec. (trace 1), 2 min. 15 sec. (trace 2), 6 min. 15 sec. (trace 3), 15 min. (trace 4), 25 min. (trac 5) and 30 min. (trace 6). It will be seen that the peak at 734 nm develops and stabilizes after about 15 min. before decreasing over longer time periods.

Example 3

Detection of myoglobin in fresh plasma using ABTS

Figure 3A:
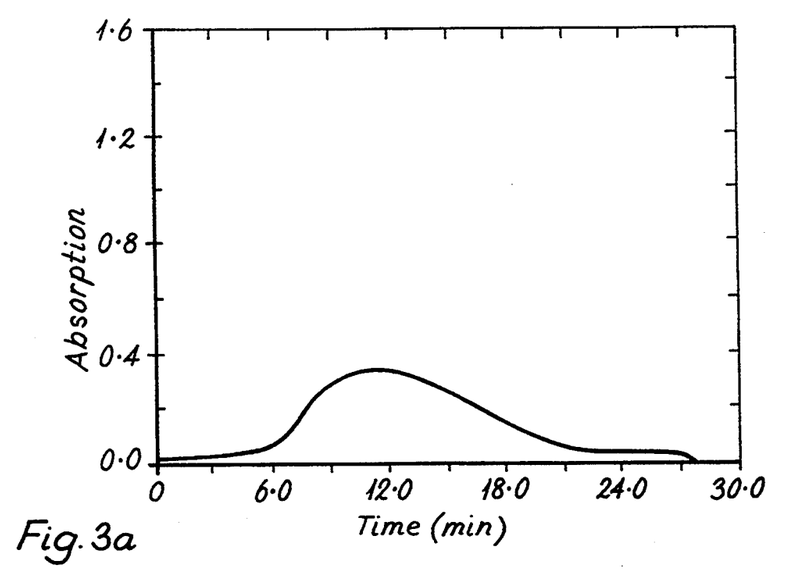
FIGS. 3a and 3b show the visible spectra obtained in accordance with Example 3 with respect to fresh plasma, and stored plasma as used in Example 2.
Figure 3B:
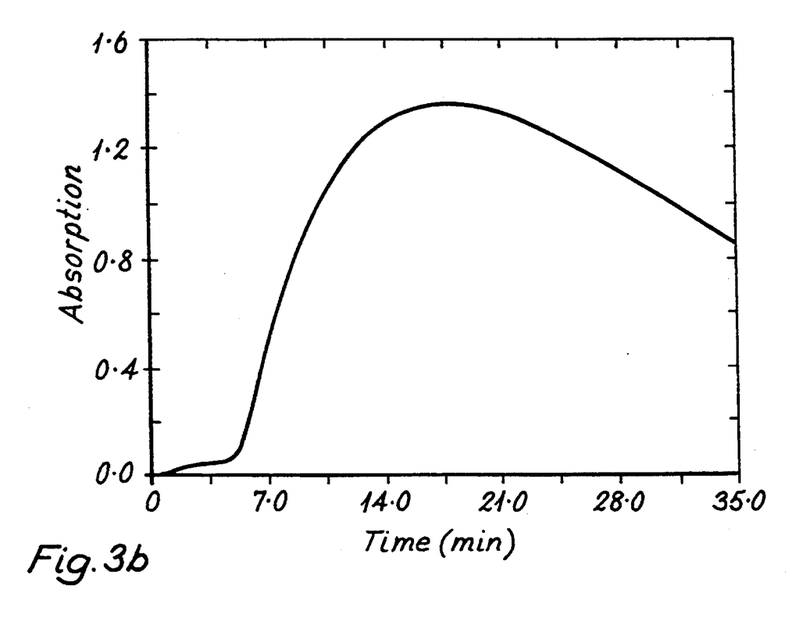

A comparison of behaviour as a function of time was made between stored plasma as used in Example 2 and fresh centrifuged plasma also obtained from a normal person. In each case 50% plasma in phosphate buffer was employed with a concentration of myoglobin of 2 $\mu$M, $H_2O_2$ of 1.5 mM and ABTS of 16.7 mM. The results showing the plot of absorbance against time are shown in FIG. 3a for fresh plasma and FIG. 3b for stored plasma. It is to be noted that fresh plasma, which, it is postulated, will contain a considerable amount of natural antioxidant, shows a lower absorbancy response and after a longer time lag than is the case for stored (more antioxidant deficient) plasma.

Example 4

Detection of myoglobin in buffer solution using TMB

Using 0.2M acetate buffer, pH 5.0, solutions were prepared as follows:

a) A control solution containing 20 $\mu$M metmyoglobin (obtained from Sigma and purified on a G15-120 Sephadex column before use), 50 $\mu$M TMB (obtained from Sigma) but no $H_2O_2$.

b) A control solution containing 20 $\mu$M metmyoglobin and 25 $\mu$M $H_2O_2$ but no TMB.

c) A control solution containing 50 $\mu$M TMB and 25 $\mu$M $H_2O_2$ but no metmyoglobin.

d) A test solution containing 1 $\mu$M metmyoglobin and 130 $\mu$M TMB and to which $H_2O_2$ was added at zero time to give a concentration of 65 $\mu$M.

e) A test solution containing 100 nM metmyoglobin and 130 $\mu$M TMB and to which $H_2O_2$ was added at zero time to give a concentration of 65 $\mu$M.

Figure 4:
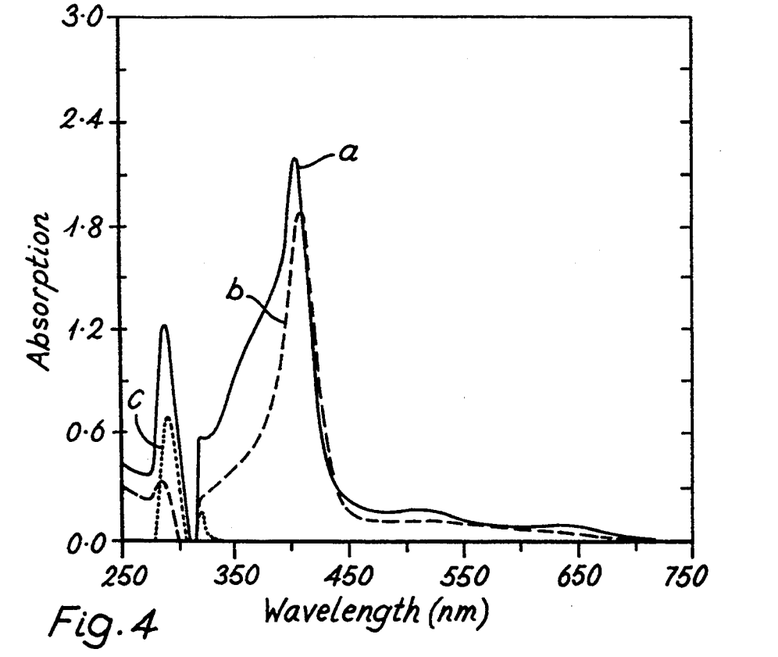
FIG. 4 shows the visible spectra for controls (a), (b) and (c) as described in Example 4.
Figure 5:
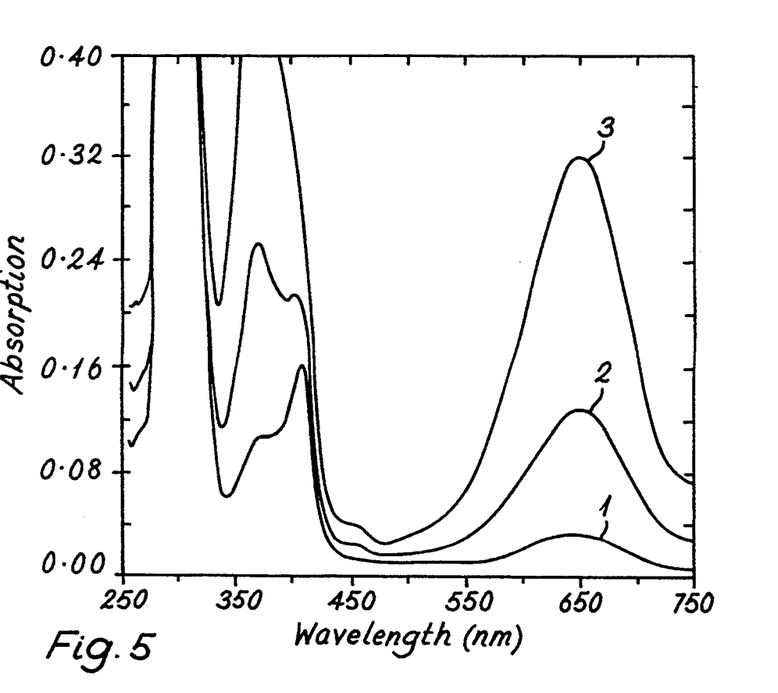
FIG. 5 shows the visible spectra for solution (d) described in Example 4.
Figure 6:
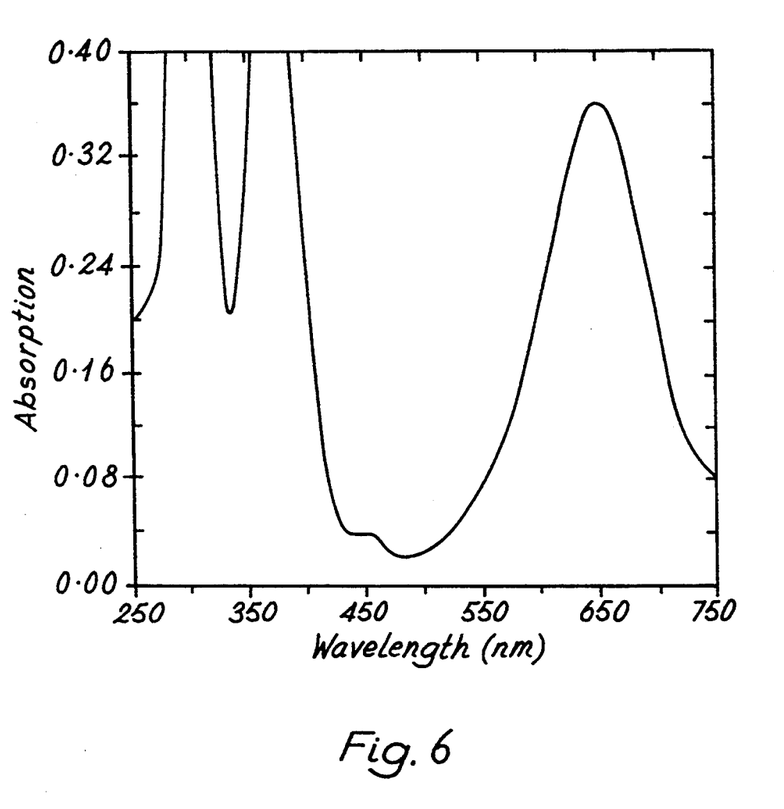
FIG. 6 shows the visible spectra for the test solution (e) described in Example 4.

The visible spectra in the range 250 nm to 750 nm were determined after given time periods using a Beckman DU65 or DU70 spectrophotometer. The results for controls a), b) and c) after a time of up to 12 minutes are given in FIG. 4. Results for test solution d) after time periods of 2, 4, and 8 minutes (traces 1, 2 and 3 respectively) are given in FIG. 5. The result for test solution e) after 2 hours is given in FIG. 6.

Example 5

Assay of total plasma antioxidant status—Optimisation of Conditions

In order to optimize the conditions necessary for assay of the antioxidant status of plasma samples in accordance with the invention. Time v absorbance measurements at 734 nm were made using a Cobas Bio centrifugal analyser at 30° C. ABTS (Aldrich) was employed in isotonic phosphate buffer pH 7.4. Myoglobin (Sigma M-1882) was employed as metmyoglobin type 111 with iron in the ferric state and purified on a G15-120 Sephadex column prior to use. The plasma samples employed were obtained by centrifugation of venous blood collected in venoject tubes for 15 min. at c. 1000 g before removal of plasma from the cells. To obtain the results, ABTS and metmyoglobin in buffer (suitably in an amount of 300 $\mu$l) and the plasma (or buffer blank) sample (from 2 to 20 $\mu$l) were mixed and the reaction initiated by the addition of, suitably, 25 $\mu$l of hydrogen peroxide after from 20 to 60 sec. incubation time. Absorbance was measured at time intervals. The development of the ABTS radical was inhibited to an extent dependent on the plasma antioxidant capacity.

a) Effect of dilution.

Figure 7:
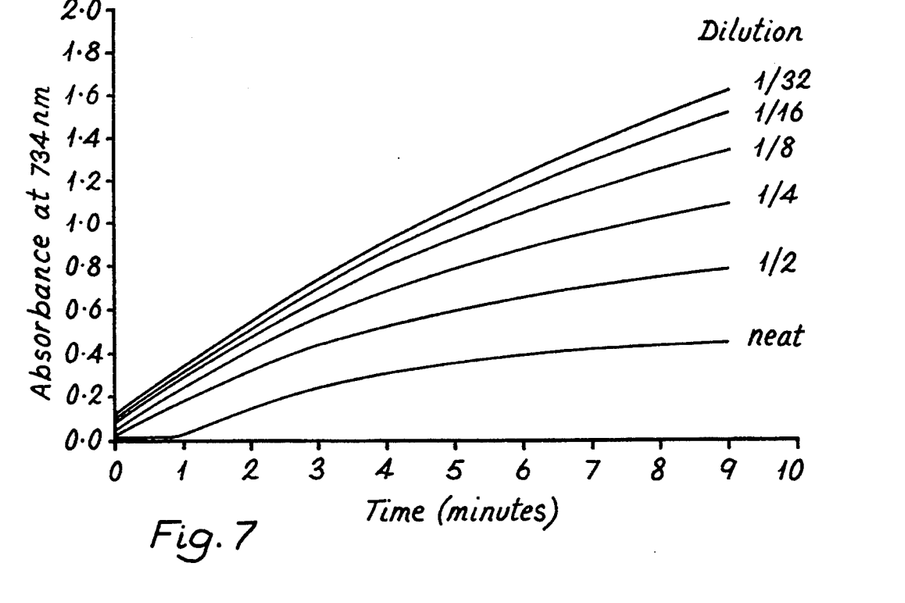
FIG. 7 shows the effect of dilution on a plasma sample as described in Example 5.

Serial dilution from neat to 1/32 was carried out on a plasma sample collected into acid citrate-dextran (ACD) and stored frozen for two months. The sample fraction was 2.7% (10 $\mu$l in 365 $\mu$l). The results using 2.5$\mu$M metmyoglobin, 250 $\mu$M ABTS and 125 $\mu$m hydrogen peroxide are shown in FIG. 7.

b) Effect of time.

Figure 8:
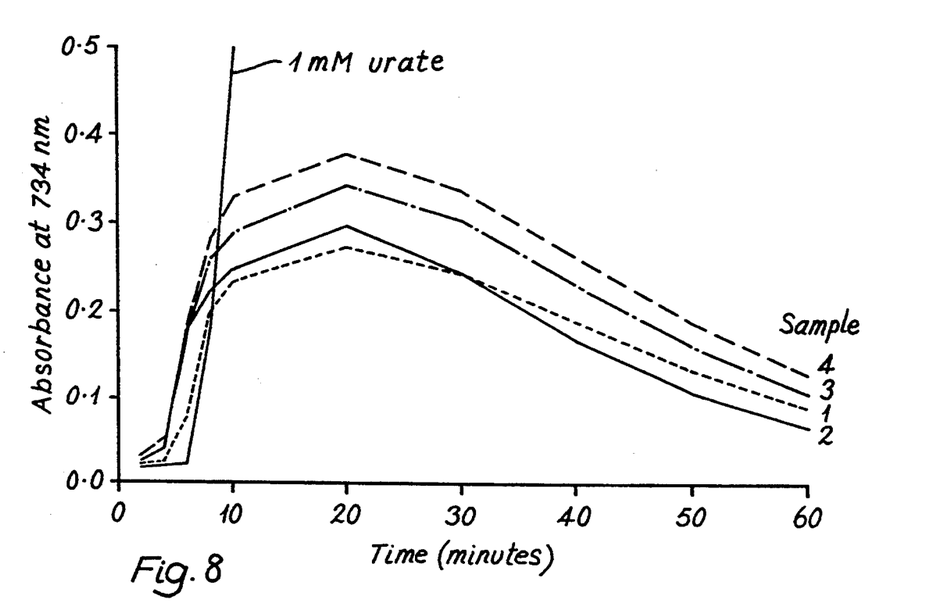
FIG. 8 shows the effect of time on samples using same concentration of reagents as described in Example 5.

Four fresh samples taken as heparinised plasma were assayed, and the absorbance change monitored for one hour. The results, using the same concentration of reagents as in a) above, are shown in FIG. 8. The samples were taken from three alcoholic patients (samples 2 to 4) and one healthy control (sample 1) in the morning, separated promptly and the plasma kept on ice, and assayed 5 hours later. There Is a slight lag phase, followed by a rapid increase In absorbance, which peaks at 10–20 minutes post mixing. There Is then a steady decline In absorbance to one hour. The sample showing the greatest absorbance (sample 4) has inhibited the reaction the least, and hence has the lowest total antioxidant activity. Sample 3 has the next highest absorbance for the one hour period, and can hence be designated as having the second lowest antioxidant activity. However the absorbance plots for sample 1 and 2 "cross over"; before 30 minutes sample 1 apparently has the higher antioxidant activity (lower absorbance), while after 30 minutes sample 2 has the higher activity (lower absorbance). For comparison purposes a plot of the absorbance of a 1 mM urate standard in buffer is shown, (it goes off scale after 10 minutes).

c) Effect of ABTS concentration.

Figure 9:
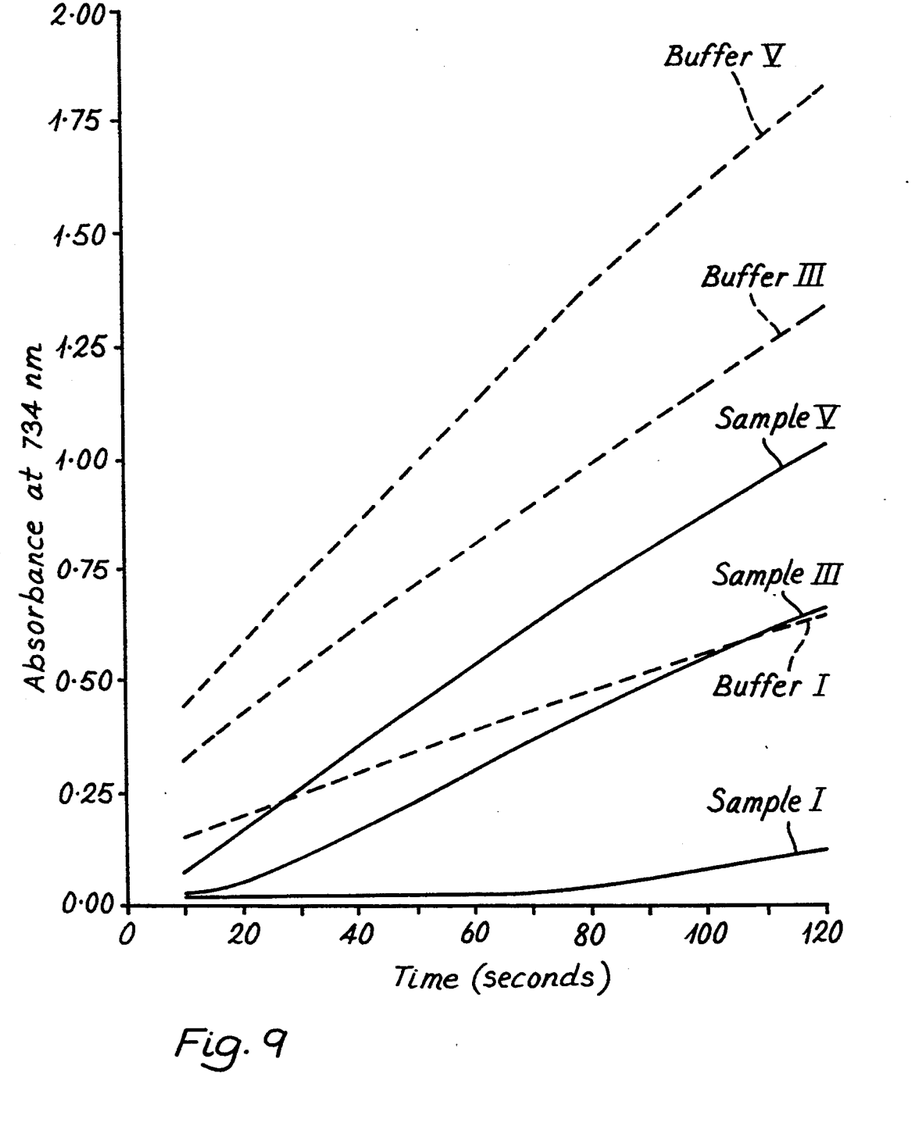
FIG. 9 shows the effect of ABTS concentration as described in Example 5.

Five sets of reagents were prepared: (i) 500 $\mu$M ABTS/250 $\mu$M H$_2$O$_2$ (ii) 1.0 mM ABTS/500 $\mu$M H$_2$O$_2$ (iii) 1.5 mM ABTS/750 $\mu$M H$_2$O$_2$ (iv) 2.0 mM ABTS/1.0 mM H$_2$O$_2$, and (v) 2.5 mM ABTS/1.25 mM H$_2$O$_2$. Concentration of metmyoglobin was 2.5 $\mu$M. The sample volume was kept at 10 $\mu$l (2.7%) and the reaction was monitored over 2 minutes. Plots are shown of time v absorbance for sets of reagents (i), (iii) and (v) in FIG. 9 for sample 1 as used in b) above, together with a buffer control in each case. The results were similar for samples 2, 3 and 4 of b) above. The results with reagents (ii) and (iv) were intermediate between (i), (iii) and (v) as expected.

d) Effect of peroxide concentration.

The effect on plasma results of varying the hydrogen peroxide concentration was investigated. 30% plasma (30 $\mu$l in 1.0 ml) and 30% plasma with 200 $\mu$M urate "spiked in" was incubated with 2.5 $\mu$M metmyoglobin, 15 mM ABTS, and a) 1.5 mM, b) 4.5 mM, and c) 7.5 mM hydrogen peroxide. There was little perceptible effect at these concentrations.

Example 6

Manual assay of total plasma antioxidant status

The following optimised concentrations of reagents as described in Example 5 were used per tube in the assay.

| Sample | 0.84% |
|---|---|
| Buffer to give an incubation volume of | 1.0 ml |
| Metmyoglobin | 2.5 $\mu$M |
| ABTS | 150 $\mu$M |
| H$_2$O$_2$ | 75 $\mu$M |

For example, a reaction tube contained:

| Sample | 8.4 $\mu$l |
|---|---|
| Buffer pH 7.4 | 489 $\mu$l |
| Metmyoglobin 70 $\mu$M | 36 $\mu$l |
| ABTS 500 $\mu$M | 300 $\mu$l |
| H$_2$O$_2$ 450 $\mu$M | 167 $\mu$l |

The reagents were mixed, by adding in the order shown, in a glass 12×75 mm culture tube and vortexed after addition of ABTS. 167 $\mu$l of hydrogen peroxide was added to start the reaction, the clock started, and the mixture vortexed again. The reaction mixture was transferred into the spectrophotometer cuvette with a plastic pasteur pipette, and scanning started (from 450 to 900 nm) at exactly 15 seconds.

The cuvette was scanned at 90 second intervals for 15 minutes. A quantitative relationship was found to exist between the absorbance at 734 nm at time 6 minutes and the antioxidant concentration of the added sample or standard. As standard there was used a solution of 2.5 mM "Trolox" (a soluble analogue of $\alpha$-tocopherol obtained from Aldrich).

Figure 10:
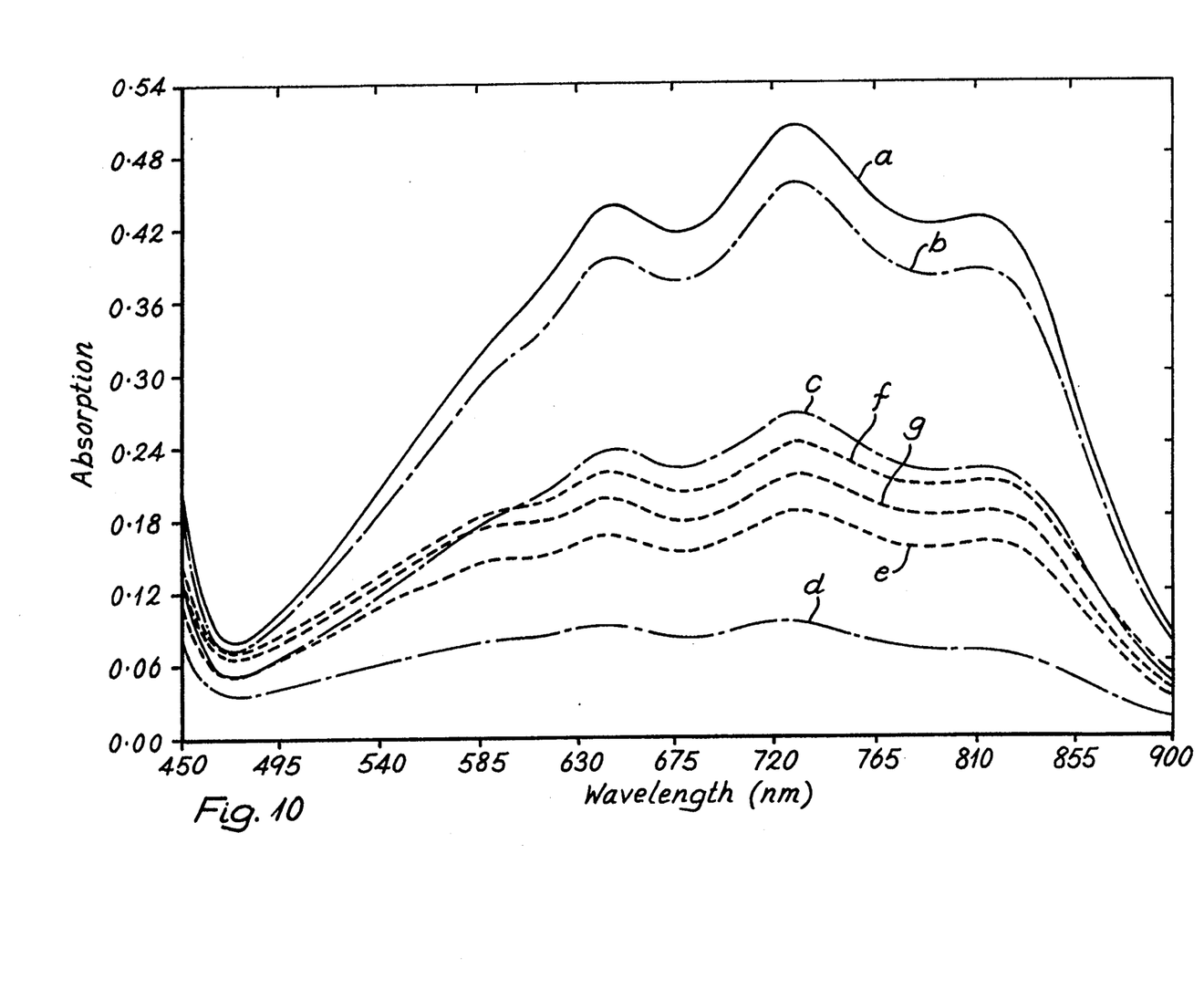
FIG. 10 shows the absorption spectra for solutions described in Example 6.

The absorbance spectra after 6 minutes are shown in FIG. 10 for a) buffer blank, b) 0.5 mM Trolox c) 1.5 mM Trolox d) 2.5 mM Trolox and e), f) and g) (which are three different plasma samples.

Example 7

Assay of Antioxidant Substances

Solutions of known or potential antioxidant substances were tested in the assay for total antioxidant activity using a Cobas Bio analyser and optimised reagent conditions as described in Example 6. The protocol was as follows: the substance was obtained in aqueous solution at three concentrations (e.g. 2.0 mM, 1.0 mM, and 0.5 mM), and an aliquot of each included as an analytical in a Cobas Bio run. This was repeated three times. A mean figure for the antioxidant capacity per mole of substance was derived, and this figure converted into a "trolox equivalent" figure. The "trolox equivalent antioxidant capacity" (TEAC) is therefore the amount of substance with an equivalent antioxidant capacity to a mole of trolox. The smaller the figure, the higher the antioxidant potential of the substance being tested: the larger the figure, the less the antioxidant potential of the substance.

The following antioxidant "ranking" was derived:

| SUBSTANCE | Trolox equivalent antioxidant capacity (TEAC) |
|---|---|
| Ascorbate | 1.00 |
| Urate | 1.00 |
| Human Albumin | 1.58 |
| Glucose | no effect (to 10 mM) |
| Heparin | no effect (to 10,000 iu) |
| Ethanol | no effect |

We claim:

1. A diagnostic test for determining the total antioxidant status of a sample, said test comprising the steps of:
  adding to the sample a known quantity of myoglobin, an oxidant for myoglobin and a compound which reacts in the presence of myoglobin and said oxidant to form a chromogenic species which demonstrates a characteristic absorption band in a region of the visible spectrum; and
  monitoring the intensity or time to maximum intensity of said characteristic absorption band to determine said total antioxidant status wherein a decreased intensity or an increased amount of time to reach maximum intensity of said characteristic absorption band indicates a greater antioxidant status of said sample 2. A test according to claim 1, wherein the compound which reacts to form a chromogenic species is 2,2'-azinobis-(3-ethylbenzthiazoline-6-sulphonic acid) or a salt thereof.

3. A test according to claim 1, wherein the compound which reacts to form a chromogenic species is 3,5,3',5'-tetramethyl benzidine.

4. A test according to claim 1, wherein the sample is a clinical sample.

5. A test according to claim 4, wherein the clinical sample is blood plasma.

6. A test according to claim 1, wherein the sample is a non-clinical sample.

7. A test according to claim 6, wherein the non-clinical sample is a drug or foodstuff.

* * * * *